United States Patent [19]

Schaffner et al.

[11] 4,035,568

[45] July 12, 1977

[54] DERIVATIVES OF POLYENE MACROLIDE ANTIBIOTICS

[75] Inventors: Carl P. Schaffner, Trenton; Witold Mechlinski, New Brunswick, both of N.J.

[73] Assignee: Rutgers Research and Educational Foundation, New Brunswick, N.J.

[21] Appl. No.: 637,090

[22] Filed: Dec. 3, 1975

Related U.S. Application Data

[62] Division of Ser. No. 152,460, June 7, 1971, Pat. No. 3,945,993.

[51] Int. Cl.$^2$ .................................. C07H 17/08
[52] U.S. Cl. ................................. 536/17; 536/115
[58] Field of Search ............... 260/210 AB, 234 R; 536/17, 115

[56] References Cited

U.S. PATENT DOCUMENTS 3,780,173  12/1973  Bruzzese et al. ............ 260/210 AB

*Primary Examiner*—Johnnie R. Brown

*Attorney, Agent, or Firm*—Cooper, Dunham, Clark, Griffin & Moran

[57] ABSTRACT

Derivatives of amphoteric polyene macrolide antibiotics which carry, on the lactone ring, a carboxyl group and an amino sugar characterized by a primary amine group, consist of (a) the methyl, ethyl or propyl ester formed by esterification of the carboxyl group, and (b) salts of such polyene esters constituted as acid addition salts formed with the amine group. The derivatives (a) and (b) have effective antimicrobial activity, e.g. antifungal potency, comparable to the base antibiotics, and the acid salts (b), produced by suitable acids, e.g. hydrochlorides, can be made to have good water solubility which is normally unattainable with the base compounds and is of special advantage in a compound which retains strong activity. Other addition salts are also of value, for example to provide lipid-soluble forms of these antifungal polyenes. Esterification of these chemically sensitive antibiotics is unusually successful using diazomethane, diazoethane or diazopropane with tetrahydrofurane as solvent to produce the ester dissolved therein, avoiding degradation of the base antibiotic or of its potency.

5 Claims, 12 Drawing Figures

BASE COMPOUND (AMPHOTERICIN B): $C_{47}H_{73}O_{17}N$

BASE COMPOUND (NYSTATIN): $C_{47}H_{75}O_{17}N$

BASE COMPOUND (PIMARICIN): $C_{33}H_{47}O_{14}N$

DERIVATIVES OF POLYENE MACROLIDE ANTIBIOTICS

The invention described herein was made in the course of work under a grant or award from the Department of Health, Education, and Welfare.

This is a division, of application Ser. No. 152,460 filed June 7, 1971, now U.S. Pat. No. 3,945,993.

BACKGROUND OF THE INVENTION

This invention relates to derivatives of polyene macrolide antibiotics and more particularly is directed to the provision of new compounds of this class, having significant advantages or characteristics while exhibiting the antimicrobial or biological activity of the underlying or base substances.

The polyene macrolide antibiotics are a well recognized class of compounds, conventionally produced by cultivation of various suitable organisms and by extraction of the substance from the culture. They are primarily recognized as antifungal agents, although in one instance or another they may exhibit significantly useful activity against other micro-organisms. The compounds are basically and uniquely characterized by a large lactone ring which includes a chain of conjugated double bonds, specifically comprising 4, 5, 6 or 7 such linkages, whereby the compounds are correspondingly known as tetraenes, pentaenes, hexaenes and heptaenes and are collectively called polyenes. Thus the base antibiotics are high molecular weight (e.g. in the range of 700–1,200) macrocyclic lactones, known as macrolides, and since they contain an amino sugar moiety, can be described as comprising an amino sugar glycoside of a macrolide nucleus that possesses a chromophore of 4 to 7 conjugated double bonds.

As a class, the molecular structure of the base compounds has been quite well defined, in that in all cases it primarily consists of a macrocyclic lactone nucleus which is a long chain of carbon atoms (e.g. in the range of 20 to 40) closed by a single lactone oxygen atoms to constitute the macrolide ring and having a carbonyl oxygen on a carbon atom of the ring immediately adjacent to the lactone oxygen, as is characteristic of lactones. The carbon atoms are directly, successively linked to each other along the ring by single or double bonds, mostly single bonds, but in all cases with the important situation of the uninterrupted series of conjugated double bonds specified above. As stated, the compound also includes a single amino sugar, linked to the ring as a substituent and carrying a free primary amine group. There are also a plurality of —OH groups which are attached respectively to a plurality of carbon atoms of the ring (other than the double-bonded atoms) and finally, in those of the polyene macrolides to which the present invention is directed, there is a single carboxyl group, also linked to the ring as a substituent. Additinal substitution is normally found, which varies among specific members of the class, but is not deemed to alter the basically unique molecular structure or indeed the fundamental characteristics of these compounds as antifungal agents. The additional substitution involves substituents of one or more types such as various alkyls, oxygen, epoxy, and in a number of cases, groups that may be designated as aryl amine moieties.

The compositions are further defined hereinbelow, including a number of specifically elucidated examples, but it will be understood that the base polyene antifungal antibiotics constitute a recognized class of substances, beig macrolides critically distinguished by the above defined composition, including particularly the stated chain of conjugated double bonds, and thus specifically distinguished from other chemical compounds, including other macrocyclic lactones.

As will be apparent, the members of the class to which the present invention is directed, being characterized by a free carboxyl group, have been recognized as amphoteric, by reason of the presence of such group and also the free amino radical in the amino sugar. Indeed the amphoteric nature of these water-insoluble compounds has contributed, as will be apparent below, to past difficulty in trying to convert them to water-soluble form.

Examples of this specific class of amphoteric antifungal antibiotics include: amphotericin A, nystatin, pimaricin and rimocidin, all tetraenes; eurocidin, a pentaene; cryptocidin and mediocidin, hexaenes; and amphotericin B, candicidin, candidin, candimycin, hamycin, levorin and trichomycin, which are heptanes.

Although the antibiotics of this class have been recognized as significantly active, chiefly against fungus organisms, and a number of such antibiotics have been extensively used and are commercially available, they have been generally limited in utility by lack of effective water solubility of equivalent dispersibility in water. In some instances so-called salts, such as sodium salts, have been produced by reaction of alkali with the carboxyl group, to yield a substance having some water solubility, but such products have only exhibited solubility at a relatively high pH and have suffered from deterioration of their stability. On the other hand, efforts to produce so-called acid salts by acid addition to the amino group have been either ineffectual or of little or no utility in that the water soluble properties are then only exhibited at undesirably low pH values and with considerable instability.

In U.S. Pat. No. 3,244,590, a class of N-acyl derivatives of the heptaene antibiotics is disclosed, which retain some anti-microbial activity and which are convertible into water soluble salts (by alkaline reaction with a carbonyl group) yielding some utility in water. It has been found, however, that in at least a number of cases, the biological activity is substantially reduced and thus while these water soluble, N-acyl derivatives have some utility, there has remained a considerable need for products useful with substantially high activity in aqueous media.

Another procedure for achieving a water dispersible composition has been exemplified by the preparation of a complex of amphotericin B with desoxycholic acid, which acts as a detergent. Complexes of this type, however, do not form true solutions; the substance appears merely to be dispersed as a colloid, and the field of utility is correspondingly limited.

In a more general sense the invention is concerned with improvement of the polyene antibiotics not only with respect to attainment of substantial water solubility, but also in relation to other possibilities of use. For example, although the base compounds are soluble in a number of organic solvents, difficulty is encountered in some circumstances of potential value, as for example where it may be desirable to carry the antibiotic in a lipid base, i.e. such as an ointment or cream having a significant fat content and desired to be substantially non-aqueous. In all of these respects, but most especially in regard to the provision of water soluble products, an important aim of the present invention, among other objects as will be apparent, is to provide new and unusually valuable derivatives of these antibiotics.

SUMMARY OF THE INVENTION

The invention is primarily predicated on the discovery: that the stated polyene substances, as defined above, can be efficiently converted to an ester, specifically a methyl, ethyl or propyl ester, by reaction under appropriate conditions, which in preferred form embody novel features of procedure as explained below; that the resulting derivative, being the stated ester, can then be converted to a further derivative, being the acid addition salt, by reaction with the free amino group of the amino sugar; and that such products, most especially the acid salt derivatives, represent new compounds of extraordinary advantage.

Specifically, the defined esters are themselves characterized by retention of antimicrobial activity comparable to that of the parent or base compound, as has been abundantly demonstrated by tests. So far as can be ascertained, it does not appear that such an ester of a polyene antifungal antibiotic has in fact been prepared prior to the present invention, nor more importantly, that the substantial biological activity of such esters has been suggested or predictable prior to the invention. Although the ester itself, which remains essentially insoluble in water is conceivably of utility in the same manner as the parent substance, its cheif usefulness is as an intermediate or starting material for preparation of the described acid salts, which can be made, for example, to have substantial water solubility to pH values at or near neutrality, i.e. greatly removed from substantial acid or alkaline conditions. As explained above, attempts to provide solubility by the route of acid addition to the parent compounds have been ineffectual, and offered no promise of success by such route, because the limited water solubility, if achieved, could in general only be exhibited at extremely low, i.e. acidic pH values, and even when with serious instability of the polyene itself.

Thus in a specific but unusually important sense the invention comprises a new class of compounds, being the water soluble, acid addition salts of a lower alkyl ester, specifically the methyl, ethyl or propyl ester, of the defined polyene macrolides. Such compounds have now been found to be characterized by substantial antimicrobial activity, comparable to the activity of the parent substance, and by true and substantial water solubility, e.g. at or near neutrality. In consequence the products are useful in a large variety of circumstances where the essentially water-soluble base antibiotics, known as potent antifungal substances, have been found inappropriate, as for example under conditions when the prevention or inhibition of the occurrence or growth of fungus and like organisms, or other attack on infection by them, requires an aqueous medium, and especially where efforts to carry the agent in nonaqueous medium have had undesirable consequences.

In a more generic sense, the novel end products, defined as the acid addition salts of the stated esters, may be embodied to have other specific utility, for example in providing fat-soluble compositions, as distinguished from water-soluble compounds, that are especially appropriate for use in corresponding lipid-based media. This is of special advantage for various ointments, creams or the like designed for topical application, and also for other purposes, e.g. agricultrual purposes as in treating fungus infections of plants, where it may be desirable to have preparations that will not be readily washed away and will have prolonged effectiveness in external surface contact.

A further, specific feature of the invention resides in certain novel procedure for preparing the ester, especially in view of the sensitivity of these polyene macrolides to many reagents. Thus ordinary esterification operations using hydrochloric acid or surfuric acid and alcohol are highly undesirable, because the required concentration of such acids tend to destroy the antifungal activity. It has now been found that among numerous other possible reagents for esterification, compounds of the class consisting of diazomethane, diazoethane and diazopropane are highly effective, and unexpectedly selective for these antibiotics, i.e. in avoiding any adverse side reactions.

A very significant feature of the process resides in the discovery of unusual advantage in employing a specific solvent, namely tetrahydrofurane, to carry out the esterification of the antibiotic with diazomethane or other reagent of its group, and indeed to carry out the preceding preparation of such reagent. Whereas ethyl ether in which diazomethane or the like is normally made and useful is relatively ineffectual because the base polyene antibiotics are essentially insoluble in it, tetrahydrofurane is suitable for both steps, especially because it is capable of sufficiently maintaining solution of these amphoteric antibiotics, initially, dissolved in dimethyl sulfoxide, for the desired ester reaction, without appreciable effect on their biological activity. In deed it appears that over a relatively short reaction time, the base antibiotic gradually goes into solution in the tetrahydrofurane, whereupon the ester is formed and collected in solution, and the completion of reaction is conveniently determinable, in effect, by the disappearance of undissolved antibiotic.

To produce the desired acid addition salt, the polyene macrolide ester is recovered from the above solution and is then treated, in water, at appropriate pH, for example not far from neutrality, with suitably dilute concentration of the selected acid, e.g. hydrochloric, sulfuric or other, as explained below.

The above procedure has been applied to a variety of base substances of the stated class, and the resulting esters have been converted to acid salts, i.e. by addition reaction with the free amino group of the amino sugar, yielding biologically active products having the improved characteristics and greatly extending utility outlined above. Thus for example, the hydrochloride salts and amphotericin B methyl ester, candicidin methyl ester, trichomycin methyl ester and various others have been prepared in a relatively high state of purity and have exhibited good water solubility. Tests of ester and salt products have clearly evidenced good antimicrobial activity of nature of the base materials. specific examples and additional detail and demonstration of the comounds and results are set forth hereinbelow, aided by illustrative information in the accompanying drawings.

BRIEF DESCRIPTION OF THE DRAWINGS

in FIG. 8, amphotericin B and its methyl and ethyl esters; in FIG. 9, nystatin and pimaricin, respectively with their methyl esters; FIG. 10, mediocidin and methyl ester; FIG. 11, hamycin and methyl ester; and FIG. 12, trichomycin and methyl ester.

DETAILED DESCRIPTION

Figure 1:
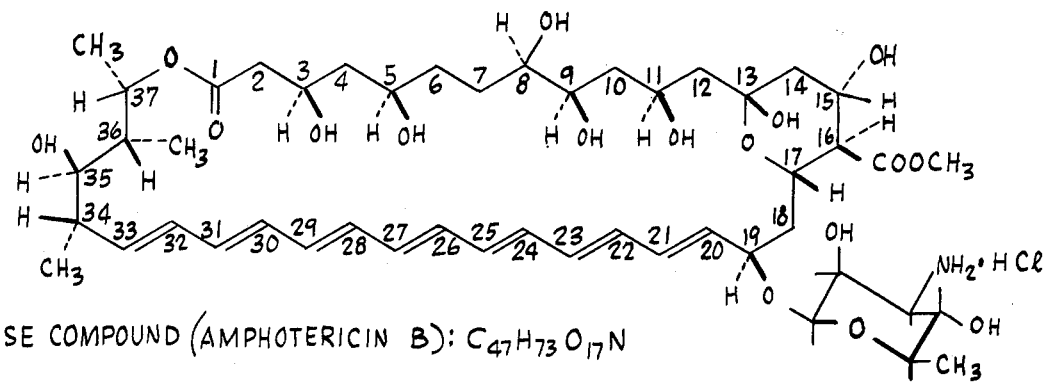
FIGS. 1, 2, and 3 are respectively structural molecular formulas, as presently understood, of three examples of products of the invention, namely the hydrochlorides of the methyl esters of amphotericin B, nystatin and pimaricin.

As indicated above, the invention relates to the stated esters of the defined class of polyene macrolides and most importantly to the acid addition salts of such esters, e.g. as prepared from base compounds such as amphotericin B, nystatin, trichomycin, mediocidin, candicidin, pimaricin, candidin, hamycin and many others.

In all cases, the presently preferred procedure for making these products is essentially the same. The required reagent, e.g. diazomethane for producing the methyl ester, is first prepared, being obtained in solution in tetrahydrofurane. Thereafter the selected polyene macrolide, preferably in initial solution in dimethyl sulfoxide is established in admixture with the diazomethane solution, plus further tetrahydrofurane as desirable, whereupon the esterification is caused to occur, and the ultimate methyl ester is thereafter precipitated and recovered in appropriate manner. Finally, the methyl ester is treated with the selected acid, e.g. hydrochloric, to obtain the desired water-soluble acid salt, which is suitably recovered, for example by lyophilization, yielding a final product of high purity, i.e. of purity comparable to the preferably pure antibiotic which was subjected to esterification.

The presently preferred procedure is best explained in detail by an example of the above sequence of steps. As will be understood, it is highly desirable to prepare substances such as diazomethane, diazoethane and diazopropane in fresh condition for prompt use in the ester reaction. They are relatively unstable, and furthermore require care in handling because of toxicity; thus the preparation of such compounds should be performed with due safety precautions because of instability and of need to provide for removal and disposal of fumes.

The specific example, set forth in relation to the preparation of derivatives of amphotericin B is as follows:

Preparation of Diazomethane 2 g. of potassium hydroxide were dissolved in 1.5 ml. of water in a 100 ml. distillation flask equipped with a dropping funnel and an efficient condenser. The solution was diluted with 4 ml. of 95% ethanol and 20 ml. of tetrahydrofurane (e.g. commercial grade, free of peroxides). The condenser was connected to a suitable receiver adapter and a 100 ml. flask as a receiver, all with appropriate provision for safe venting. The receiver flask was cooled in ice. After heating the contents of the distilling flask to slow boiling, there was introduced through the dropping funnel a solution containing 8.3 g. of p-tolylsulfonylmethylnitrosamide (which is one of the known precursors or starting materials for diazomethane) in 30 ml. of tetrahydrofurane, adjusting the rate of addition so that it was about equal to the rate of distillation. The diazomethane which was produced in dissolved form in tetrahydrofurane distilled off with the latter and condensed as a yellow liquid in the receiver. After emptying the dropping funnel, a further quantity (10 ml.) of tetrahydrofurane was added in the same manner as before in order to remove the rest of the product from the reaction mixture. The distillation was considered complete when the distillate turned colorless. After first getting the reaction flask cooled down in ice, the chilled receiver was removed and found to contain about 1.0 - 1.2 g. of diazomethane in about 40 ml. of tetrahydrofurane. It was kept in ice until used. Indeed because of the instability of this reagent it should ordinarily be used the same day for esterification of a polyene macrolide such as amphotericin B.

Preparation of Amphotericin B Methyl Ester 1.0 g. of amphotericin B (Squibb; high purity, assay 972 mcg./mg.) was dissolved in 10 ml. of diemthyl sulfoxide using a tissue grinder. The solution was transferred to a 100 ml. erlenmeyer flask with the help of 10 ml. of tetrahydrofurane, thus used for dilution. The flask was supplied with a magnetic bar for stirring by conventional external magnetic means, and was kept cooled to 0° C. in ice while stirring. A substantial proportion of the amphotericin B was precipitated during this process, and such precipitation was found (in repeated tests) to be normal. To the stirred and cooled (0° C.) mixture, freshly prepared diazomethane solution in tetrahydrofurane (as above) was slowly added, using a total of 15 ml. in about a 10 minute period. During this time the amphotericin B dissolved and the esterification was effected and completed; if desired, completion of reaction can be checked by thin layer chromatography, performed as explained below.

The product is preferably isolated at once, to avoid side products. For such purpose the reaction mixture was diluted with 15 ml. of dry methyl alcohol, and poured slowly into 250 ml. of dry ethyl ether stirred with a magnetic stirrer. Stirring was continued for about 5 minutes, and the precipitate was then removed by centrifugation. The supernatant was discarded (although it can be treated to recover additional product if desired), and the precipitate was washed with 50 ml. of dry ether, followed by centrifugation again. This separation was advantageously repeated two times more, and the product was dried under vacuum. The yield was 850–900 mg. of a gold-yellow powder, determined to be the desired methyl ester of amphotericin B.

Preparation of Amphotericin B Methyl Ester Hydrochloride

A quantity e.g. 1.6 g., of amphotericin B methyl ester (produced by syntheses as described above) was suspended in 50 ml. of ice cold water using a tissue grinder. The suspension was transferred to a 100 ml.

erlenmeyer flask equipped with a magnetic bar for stirring and was stirred in an ice bath to lower the temperature to about 0° C. While stirring there was added slowly, from a dripping funnel, 0.1N hydrochloric acid in water in sufficient amount and at sufficient rate that the pH of the reaction mixture was kept between 6 and 5. The suspended methyl ester was found to go slowly into solution. When the mixture would not take more acid, i.e. when further slight addition of acid did not further diminish the apparent content of undissolved matter, the process was deemed to be finished. The pH preferably had a value of 6 at this point, and it was found that about 15 ml. of the dilute acid solution was used. It was found inadvisable to allow the pH to drop below 5 at any time. Some undissolved solids remained and they were removed by centrifugation and discarded as impurities; indeed in this way any unreacted amphotericin B contaminating the methyl ester is removed, so that the procedure affords a further stage of purification. The supernatant solution containing the salt product was diluted to about 150 ml. with water, and was lyophilized, i.e. dried at low pressure under freezing conditions. The yield was 1.5 g. of a golden yellow product, consisting of the desired acid addition salt, i.e. the hydrochloride of amphotericin B methyl ester, as depicted in FIG. 1.

Figure 4:
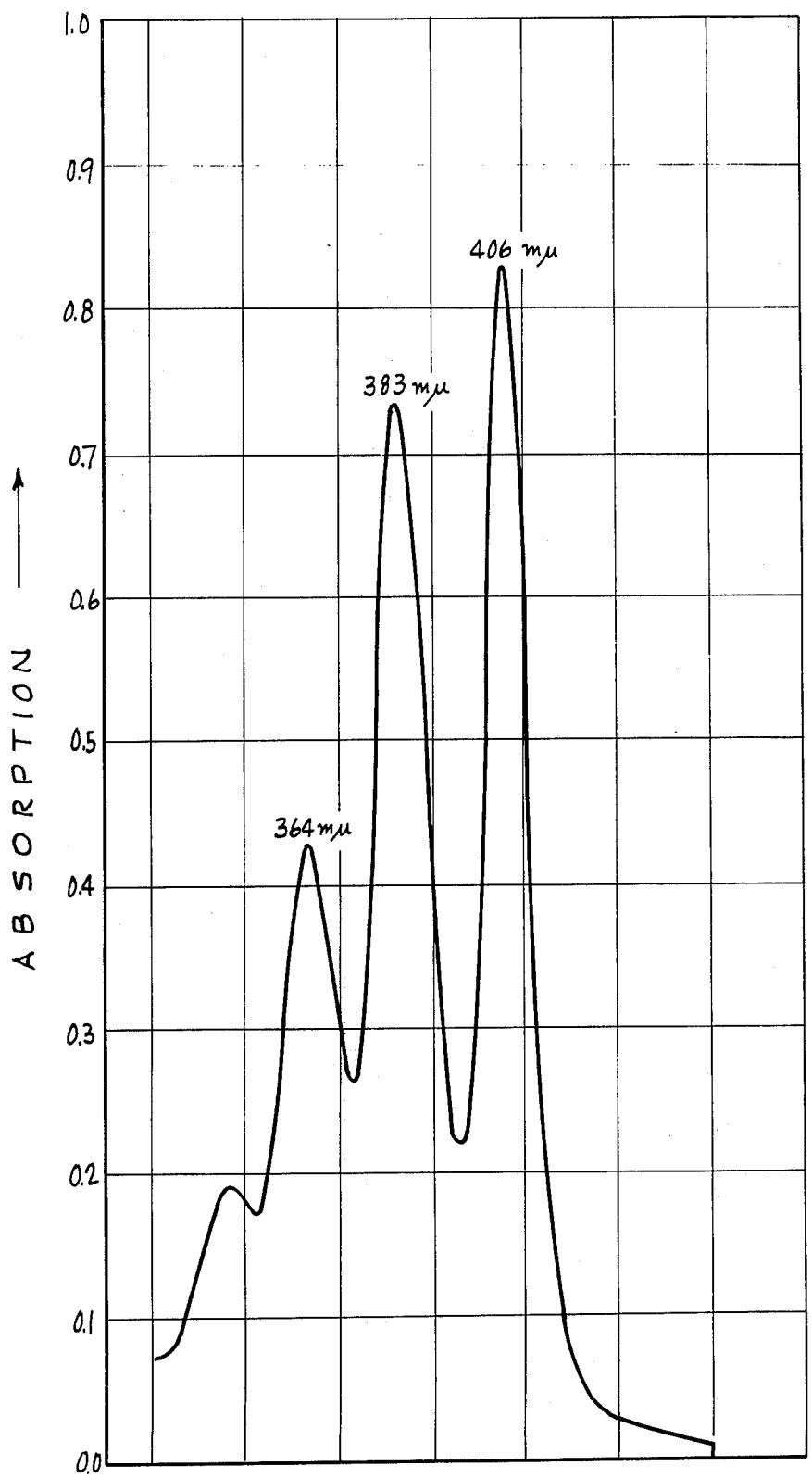
FIG. 4 is an ultra-violet spectrum of amphotericin B methyl ester.

The properties of amphotericin B methyl ester, e.g. the derivative as prepared prior to formation of the acid salt, were found to be as follows:

The ester is soluble in methyl alcohol, ethyl alcohol, tetrahydrofurane, dimethyl formamide and dimethyl sulfoxide. It is slightly soluble in ethyl acetate and in water, and insoluble in petroleum ether and ethyl ether. The substance has no melting point and decomposes steadily upon heating, with decomposition becoming rapid above 175° C. It exhibits the typical light absorption of heptaenes, as shown by its ultra-violet spectrum in FIG. 4, with major absorption maxima at 364, 383 and 406 millimicrons. This spectrum was made and plotted in conventional manner, using amphotericin B methyl ester exactly as produced in the above example, in solution in methanol in concentration of 5 micrograms per milliliter. The specific extinction of such product (without further purification) determined in standard fashion as $E_1^{1\%}$ cm., was 1480, and in comparison with the value of 1680 for the base, pure amphotericin B showed that the product ester was 88% pure. As explained above, substantial further purification can be attained, for example, in making and recovering the acid addition salt.

Figure 6:
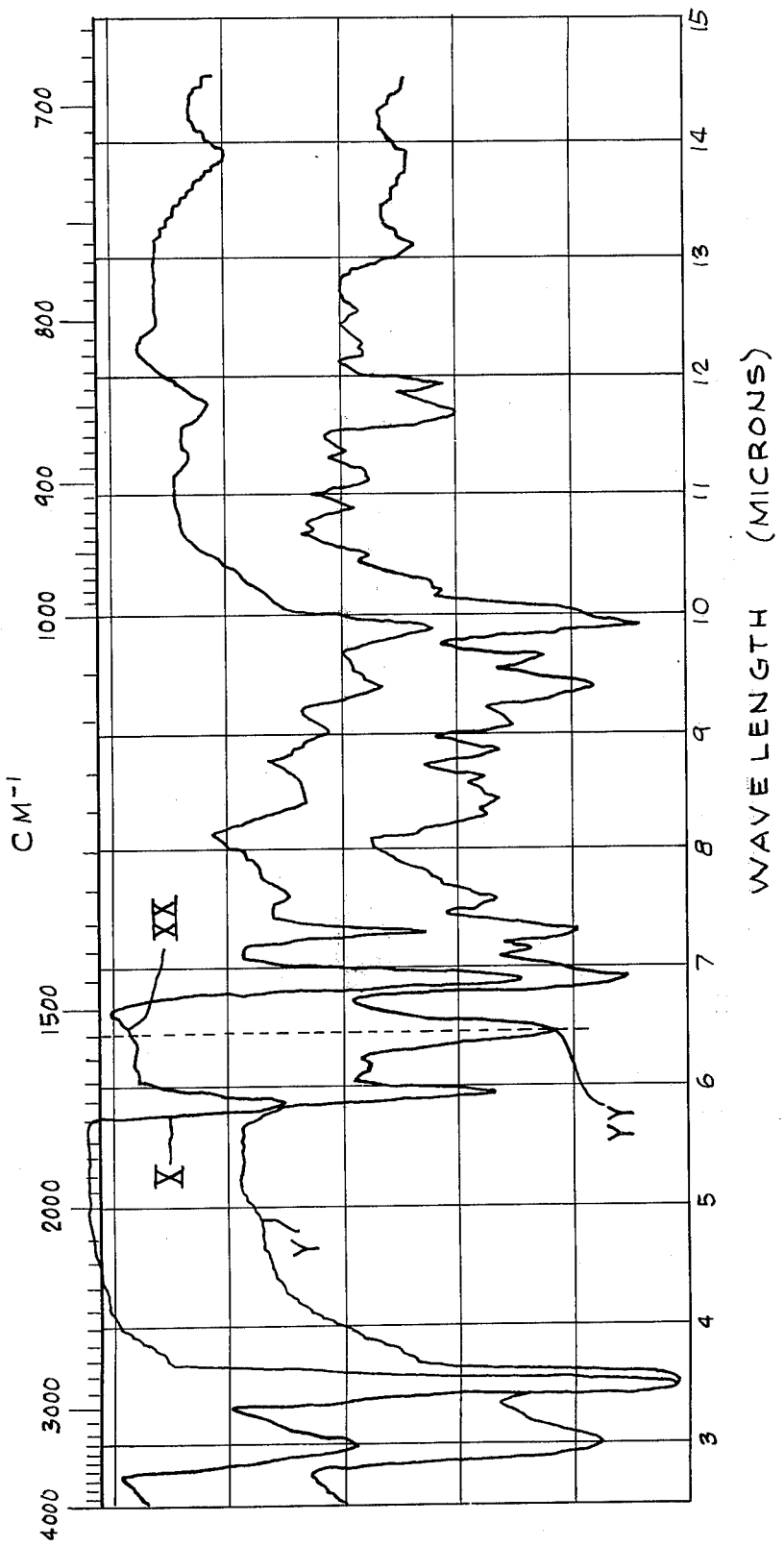
FIG. 6 is a graph showing the infra-red spectra of the base substance amphotericin B and its methyl ester, superposed on the same graph.

The infra-red absorption spectrum, shown at X in FIG. 6, of the methyl ester product obtained in the above example when compared with a similar spectrum of the pure amphotericin B, shown at Y in the same graph, indicates clearly the conversion of the carboxyl group of amphotericin B into an ester group. The very characteristic band for an ionized carboxyl group COO— present in amphotericin B as anti-symmetrical vibrations at 1540 cm.$^{-1}$ shown at YY of curve Y in FIG. 6 vanishes completely in the spectrum of the amphotericin B methyl ester, as apparent at XX of curve X. It will be understood that these infra-red spectra were made in conventional fashion, but are displayed in arbitrary vertical spacing in FIG. 6 so that although the configurations are as recorded, the actual percent transmittance values are omitted to avoid confusion. It is also understood that the lack of some fine structure in the curve (X) for the ester is attributable to its slightly impure state but does not affect the significance of demonstration of esterification.

The lack of a free carboxyl group in the esterification product was also confirmed by quantitative titration with sodium hydroxide solution at low temperature. Under similar conditions 1 mol. of amphotericin B consumed 1 mol. of sodium hydroxide, whereas the methyl ester consumed none. As explained below, the amphotericin B methyl ester separates very well from amphotericin B by means of thin layer chromatography on silica gel; the ester moves distinctly faster than the base compound.

The ultimate hydrochloride is a solid product, exhibiting substantial water solubility, e.g. upwards of 75 mg. per ml., as contrasted with the base substance, amphotericin B, for which true water solution appears to occur to no more than the trace extent of 0.0017 mg. per ml. at best. Both the ester and its hydrochloride salt exhibit very substantial antimicrobial activity, essentially the same, i.e. quantitatively, as the base antibiotic. The activity was revealed by standard in vitro tests of each derivative and the base, against representative organisms such as Saccharomyces cerevisiae, Candida albicans and Aspergillus niger. These results are in part tabulated hereinbelow, along with a number of other products of the invention, thus indicating the utility of the substance.

By essentially identical procedure to that set forth in the above specific example, so that actual description of the operations need not be recited and reference to the substances alone will constitute corresponding examples, the following further derivatives have been prepared and found to have corresponding properties as set forth in separate tables hereinbelow: Nystatin methyl ester and its hydrochloride (tetraene): pimaricin methyl ester and its hydrochloride (tetraene); mediocidin methyl ester and its hydrochloride (hexane); candicidin methyl ester and its hydrochloride (heptaene); trichomycin methyl ester and its hydrochloride (heptaene); candidin methyl ester and its hydrochloride (heptaene); hamycin methyl ester and its hydrochloride (heptaene); and as further mentioned below, amphotericin B ethyl ester and its hydrochloride (heptaene).

Figure 2:
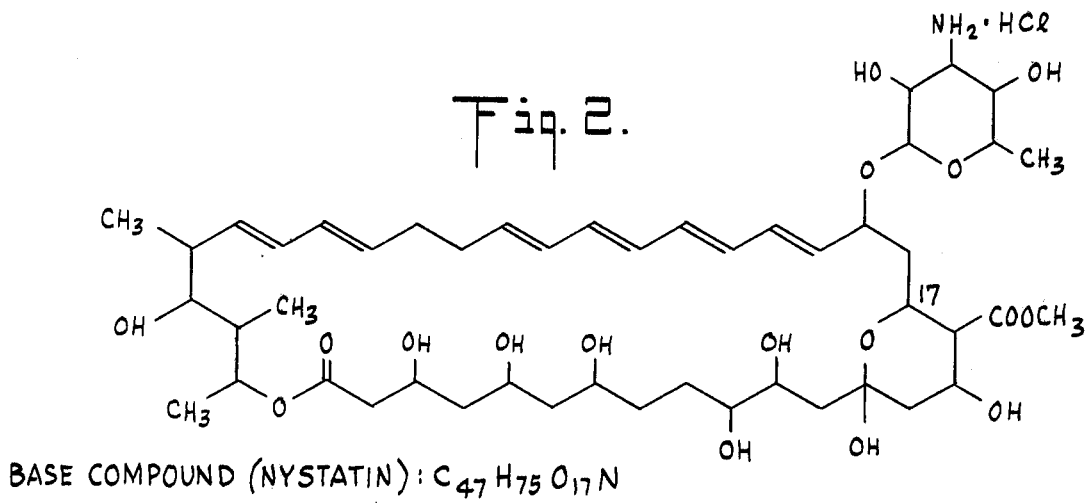
Figure 3:
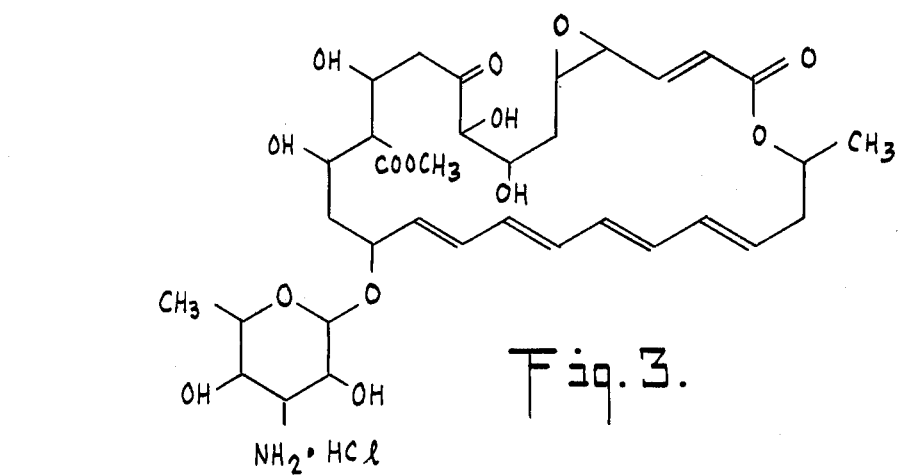

By way of further illustration of the new compounds, and indeed also of the molecular structure of the base antibiotics of this class as reported in the literature, FIGS. 1, 2 and 3 show the structural formulas for the hydrochlorides of methyl esters prepared respectively from amphotericin B, nystatin and pimaricin. It will be observed in each case that the polyene macrolide substance is characterized by the stated lactone ring, and that substituent —COOH of the base substance has been esterified to convert this moiety into an ester group —COOCH$_3$. Likewise the free amine —NH$_2$ which characterized the amino sugar, e.g. mycosamine as linked to position 19 in FIG. 1, is now converted to the addition salt form, here for example —NH$_2$.HCl. The presence of like ester and acid salt groups will be apparent from inspection of the other compounds depicted in FIGS. 2 and 3 respectively. As will also be noted, amphotericin B (FIG. 1) is a heptaene, while nystatin and pimaricin are tetraenes (FIGS. 2 and 3); the base formulas, of course, are as would appear without the two modifications described.

The reagents for preparation of ethyl and propyl esters, namely diazoethane and diazopropane, are conveniently prepared in a manner identical to diazomethane, e.g. in solution in tetrahydrofurane, using respectively appropriate starting compounds as known for these agents. Correspondingly these alternative esters of the base polyene macrolides are produced in the same way as the methyl esters, e.g. starting with a solution of the antibiotic in dimethyl sulfoxide and then mixing such solution with the principal solvent tetrahydrofurane, carrying the specific reagent, i.e. diazoethane or diazopropane. Finally the resulting ethyl or propyl ester of the macrolide is converted to the desired acid salt by operation identical with that for the methyl ester. Indeed, it is understood that the several reactions are fully analogous, and indeed identical in the case of the final salt forming operation.

Figure 7:
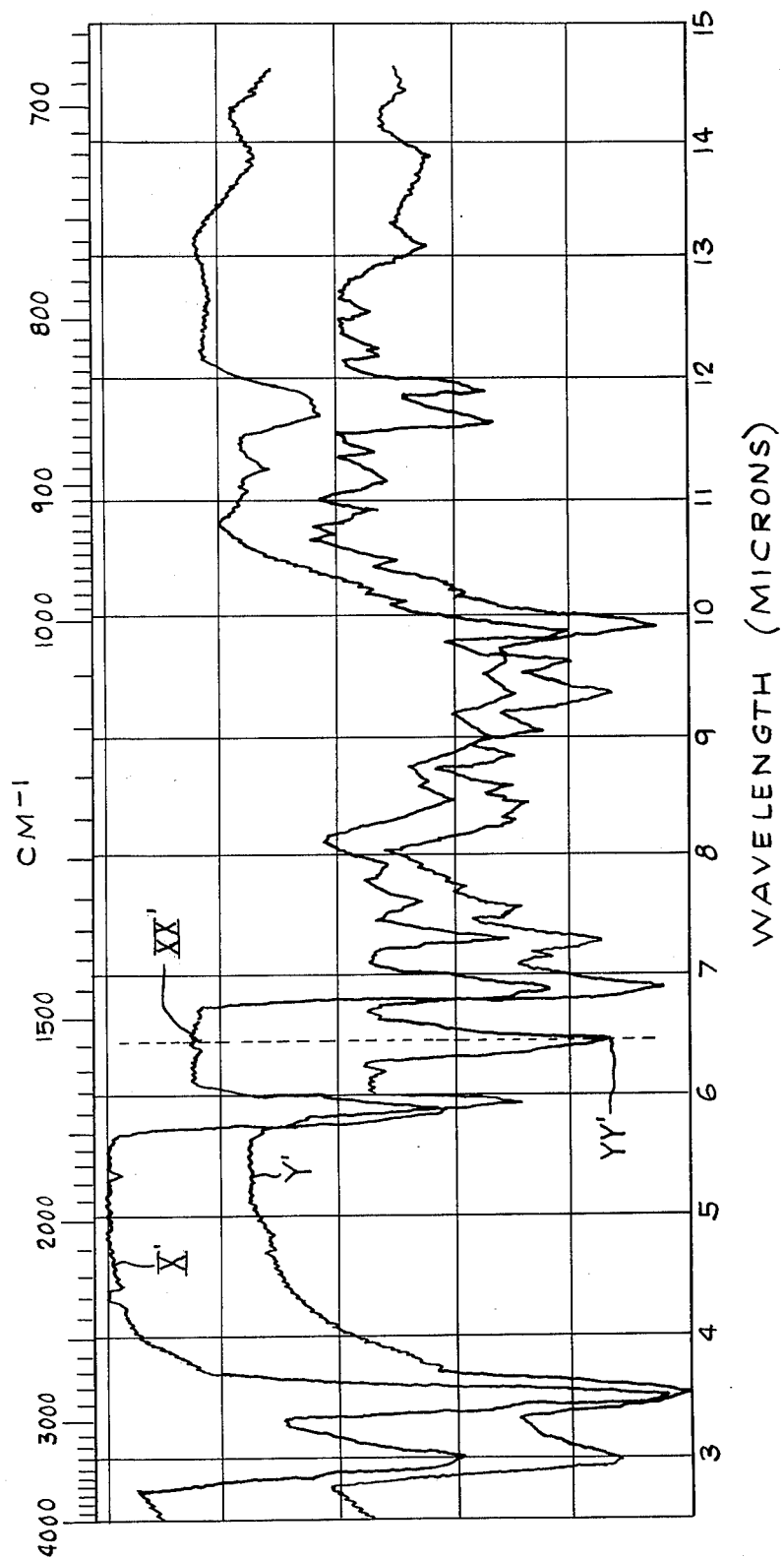
FIG. 7 is a similar graph showing the infra-red spectrum of amphotericin B ethyl ester, and for comparision, the spectrum of the same base amphotericin B.

By way of specific example amphotericin B ethyl ester and the hydrochloride salt of that derivative have been prepared in the described manner, yielding products which have properties extremely similar to the methyl ester and its salt. FIG. 7 shows the infra-red absorption spectrum of the ethyl ester (X') in comparison with the repeated spectrum of pure amphotericin B (Y'), in the same fashion as the methyl ester in FIG. 6. These again clearly demonstrate the conversion of the carboxyl group into an ester group, by disappearance at XX', of the band at YY' in the base curve.

Referring to further examples of methyl esters of other macrolides of the stated class, infra-red spectra of nystatin and pimaricin, both tetraenes, have been prepared for the base substance and the methyl ester, likewise of mediocidin, a hexaene, in the base and methyl ester forms and finally for hamycin and candicidin, and their methyl esters. In all cases, the same distinctions between the base compound and the ester were apparent, including disappearance of the bands that characterized the carboxyl group in each case, thus correspondingly establishing the fact of preparation of the ester.

Figure 8:
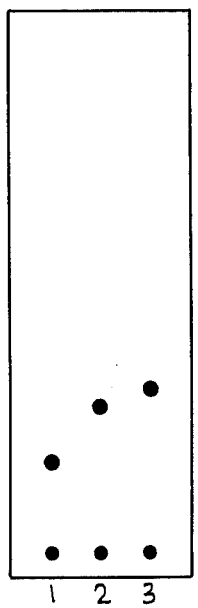
FIGS. 8 to 12 inclusive are line drawings copied from photographs of thin layer chromatograms, respectively indicating the different chemical identities of the base antibiotics and their esters, the specific substances being as follows.
Figure 9:
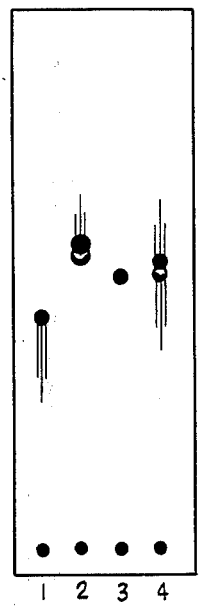
Figure 10:
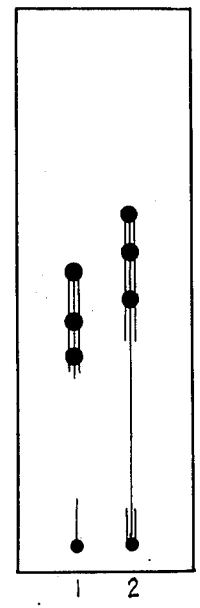
Figure 11:
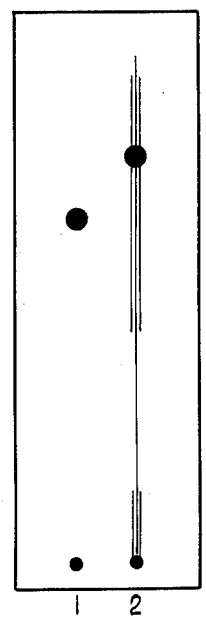
Figure 12:
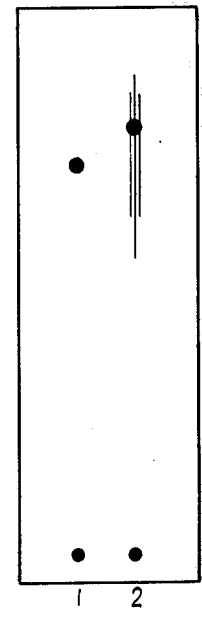

Further demonstration of the formulation of the new compounds, i.e, the esters, has been afforded by thin layer chromatography (often called T.L.C.) as shown in FIGS. 8 to 12 inclusive. As will be understood, chromatographic development by this method affords advance of each compound at a rate of characteristic of its chemical composition, so that after a selected time, the spot representative of the compound will appear at a distance from the base line on the layered plate, which is different from that of another but different compound of even closely similar composition. In FIG. 8 the base amphotericin B and the derivatives, being the methyl ester and the ethyl ester, are respectively shown in columns 1, 2 and 3. In FIG. 9, nystatin is indicated in column 1, its methyl ester in column 2, pimaricin in column 3 and its methyl ester in column 4. Columns 1 and 2 of FIG. 10 show respectively mediocidin and its methyl ester; the appearance of three spots at the upper end of each column indicates that this macrolide is, as presently available, a complex i.e. presumably involving three very slightly different compounds, e.g. such as slight differences in minor substituents on the macrolide ring. In FIG. 11, columns 1 and 2 respectively represent hamycin and its methyl ester, while in FIG. 12, at columns 1 and 2, trichomycin and trichomycin methyl ester are shown. In all cases, a substantial difference is apparent, again confirming the formation of the ester from the base substance.

The T.L.C. procedure used in these tests was essentially conventional, employing a thin layer of silica gel with appropriate binder, on a glass plate. The solvent employed for carrying the selected compounds up the layer of silica gel absorbent was selected among systems known to be suitable, from experience, for polyene antibiotics. In each instance, the selected solvent system was initially prepared as a mixture, and after shaking, the mixture separated into two phases of which the lower was employed. In FIG. 8, an alkaline solvent system derived from chloroform, methanol and borate buffer to provide a pH of 8.3 was employed. For confirmation an acidic system, being chloroform, methanol and sodium acetic buffer at pH 5.0 was independently used, with identical results. For the test of FIG. 9, the solvent system was chloroform, ethanol and 10% acetic acid; for FIG. 10 the chloroform, methanol and borate buffer system was again employed, while for FIGS. 11 and 12, a chloroform ethanol, acetic acid system was used. In each instance, a spot of each tested compound was first applied near the lower edge of the plate, e.g. from solution in dimethyl sulfoxide, and after drying and insertion of the lower edge into the selected solvent phase, development was allowed to proceed for a selected length of time, with the results shown in the drawings and described above, the appropriately advanced spots of the several compounds being readily recognized in conventional manner.

Referring further to the esterification operation, it will be understood that the basic reaction of diazomethane for producing the methyl ester of a carboxylic acid is well known, and likewise various precursors for making diazomethane ($CH_2N_2$) including the specific starting material mentioned above. For example, reference being made to a paper identified as Item 1 in the tabulation of source literature at the end of this specification. Although previous operations, as for making the reagent, have involved a conventional ether-alcohol solution (as in the cited literature), the novel operations describe herein, both for preparing the reagent and for its use in esterification, employing tetrahydrofurane as solvent, have significant advantages without interferring with the desired reactions in either stage. Although the solubility of the base macrolide antibiotics in this solvent is relatively limited, it is sufficient and indeed very appropriate for progressive esterifying reaction, yielding the ester which goes into complete solution as it is formed.

As also explained above, diazoethane and diazopropane are similarly made and are capable of effecting esterificaton, i.e. by basically known modes of reaction. For the present procedures, tetrahydrofurane is again used as the solvent in both stages, with the same effectiveness and advantages as in the case of diazomethane. It will be understood that appropriate starting reagents are employed for making diazoethane and diazopropane as explained in the literature; thus in the case of diazoethane the starting material is conveniently N-ethyl-N-nitroso-N-nitroguanidine. Underlying data on making and using diazoethane appears in Item 2 cited in the source literature below, and a further reference dealing with all three of the esterifying reagents is listed as Item 3.

The following is a list of polyene macrolide antibiotics, being all of basically antifungal potency, that are demonstrably appropriate for conversion to the novel derivative forms herein described, including the esters and the important acid addition salts of the latter. Indeed in each instance such has in fact been demonstrated by making the methyl ester and identifying the production of such compound by one or more of the modes of thin layer chromatography or infra-red spectrum. In each instance, indeed as confirmed by actual test in a considerable number of cases, the produced ester is capable of conversion into the acid addition salt (such as the hydrochloride or other salt as explained elsewhere herein), so that the described ester products of all members of this list of amphoteric compounds can be deemed examples of the invention.

TABLE I

| Name | Type | Reference Item |
| --- | --- | --- |
| Nystatin | tetraene | 4 |
| Pimaricin | tetraene | 5 |
| Rimocidin | tetraene | 6 |
| Antibiotic PA-166 | tetraene | 7 |
| Amphotericin A | tetraene | 8 |
| Chromin | tetraene | 9 |
| Eurocidin | pentaene | 10 |
| Mediocidin | hexaene | 11 |
| Cryptocidin | hexaene | 12 |
| Amphotericin B | heptaene | 13 |
| Levorin (antibiotic 26/1) | heptaene | 14 |
| Ascosin | heptaene | 15 |
| Candicidin | heptaene | 16 |
| Candidin | heptaene | 17 |
| Candimycin | heptaene | 18 |
| Hamycin | heptaene | 19 |
| Trichomycin | heptaene | 20 |
| Aureofungin | heptaene | 21 |
| Ayfactin A & B | heptaene | 31 |
| Heptamycin | heptaene | 32 |

Still further amphoteric polyene macrolides, to which the invention is deemed applicable, are the following:

TABLE II

| Name | Type | Reference Item |
| --- | --- | --- |
| Protocidin | tetraene | 22 |
| Lucensomycin (Etruscomycin) | tetraene | 23 |
| Tetrin | tetraene | 24 |
| Antibiotic PA-153 | pentaene | 25 |
| Antibiotic 2814-P | pentaene | 26 |
| Endomycin B | hexaene | 27 |
| Antibiotic PA-150 | heptaene | 28 |
| Antibiotic F-17-C | heptaene | 29 |
| Mycoheptin | heptaene | 30 |

The item numbers following the compounds in Tables I and II refer to items in the source literature list hereinbelow, respectively relating to at least one identifying description of the given antibiotic, it being nevertheless understood that all of these are known, and indeed in a number of cases reported by considerable other literature.

In all instances, the macrolide compounds from which the present derivatives are obtainable, are of a well defined general molecular structure, well exemplified by the formulas of the derivatives in FIGS. 1, 2 and 3. The basic characterization of the molecule is a macrocyclic lactone nucleus which is a long chain of carbon atoms closed by a single lactone oxygen atom to constitute the macrolide ring. A further characteristic of a lactone is also present, namely a carbonyl oxygen atom attached to a carbon atom of the ring that is immediately adjacent to the lactone oxygen. The ring carbon atoms are directly successively linked to each other along the ring by single or double bonds, but a critical characteristic of the compound is the inclusion in the ring of an uninterrupted series of 4—7 conjugated double bonds, thereby linking an uninterrupted series, respectively, of 8 to 14 carbon atoms each having one double bond linkage.

The remaining carbon to carbon linkages in the ring are very predominantly single, saturated bonds (as are the intermediate linkages in the conjugated series), although in the case of some compounds other unsaturated bonds, i.e, double bonds may appear. For example in the case of nystatin, FIG. 2, two further double bond linkages exist, spaced from the characterizing polyene series, whereas in amphotericin B, FIG. 1, all of the remaining linkages are single bonds. The total number of carbon atoms is always more than twice the number of same in the conjugated series and is generally a number within the range of 25 to 40, being indicated for example to be 37 for amphotericin B, 37 for nystatin, and 25 for pimaricin.

In every case of the polyenes here concerned, there are two significant substituents, respectively a carboxyl group (–COOH) and an amino sugar group, as apparent from the formulas given in FIGS. 1, 2 and 3. While most commonly, the amino sugar group, which in all cases is characterized by a free primary amine (–NH$_2$), is mycosamine, other amino sugars have been noted in some compounds, without difference in effect so far as basic characteristics are concerned and particulary so far as might concern the present invention, which simply requires an amino sugar moiety having the specified free amine in correspondingly significant condition of alkalinity. Some polyene macrolides, of antifungal nature, such as filipin, fungimycin, and perimycin, do not have a carboxyl group, and they are therefore not members of the class to which the invention is directed.

As will be apparent the ring is variously characterized by other substitution, which is understood to account for differences among the various polyene macrolide antibiotics, but such variation in substituents does not alter the essential characteristics of the compounds, or their suitability for conversion to the novel derivatives herein described. For example, all of the compounds are characterized by hydroxyl (—OH) substituents at various localities along the ring, e.g. usually five or more as will be apparent from the drawings. In some instances another amino substituent is present, specifically capable of classification as an aryl amine, as indicated in the composition of trichomycin; more particularly the aryl amine in the case of trichomycin is specifically identified as a para amino phenyl group, being para amino acetophenone. Other aromatic amine moieties appear in other compounds; for example in hamycin, such substituent group is that of pra amino phenyl ketone. Although it is conceivable that the acid salt formation in the present invention may extend to the amine group of such aromatic substituents, this is not understood to be of significance; the acid salt formation is primarily concerned with the more strongly alkaline amine, in the amino sugar.

Other substitution on the macrolide ring is deemed of essentially minor consequence, notably for the reactions and products herein involved, and essentially consists of one or more moieties selected from the class consisting of lower alkyl, hydroxylated lower alkyl, oxygen and epoxy, the term lower alkyl being understood to represent alkyl groups up to seven carbon atoms. Most commonly, the alkyl substitutions are simple methyl groups, usually at least several of them as in the case of FIGS. 1 and 2.

As will be noted in the figures, oxygen substitution may be simple, as in the nature of a ketone oxygen, or it may be present in bridging relation by linkage to two non-successive carbon atoms, thus in the case of amphotericin B and nystatin forming a closed, six-member configuration ecognized as a hemi ketal. In other cases, there may be similar bridging by alkyl or hydroxylated alkyl substituents. As stated, an epoxy group appears in some compounds, for example in pimaricin (FIG. 3), as a substituent on the ring. There can be duplicate or multiple substituent groups of given types, as usually in the case or —OH and methyl (—CH$_3$) groups, and indeed even for more complex groups, as with the presence of a second carboxyl group (which would then also be identically esterified), but in all cases there is no difference in the fundamental nature of the base compound as a member of the stated polyene macrolide class and no effect on the applicability of the present invention.

In general, of course, the otherwise unoccupied bonds of the carbon atoms of the ring are occupied by protons, i.e. hydrogen atoms. Indeed for the most part these are omitted from the structural drawings (FIGS. 1 to 3), it being readily apparent where they belong, i.e. at unfilled linkage lines at some places and on the ring carbons wherever unfilled bonds are evident. Of course, as is conventional for simplicity, actual designation of ring carbons is omitted, for example at positions 1 to 37 and in the sugar ring in FIG. 1. The latter figure is drawn to illustrate three-dimensional characteristics, but FIGS. 2 and 3, in simpler flat representation, are believed to be sufficiently complete in setting forth the formulas as presently understood.

Although for purposes of convenience and illustration the water soluble salts have been chiefly tested as hydrochlorides, any of a large number of other acids may be employed for making addition salts, with equally useful effect, the mechanism of forming an addition salt with a suitably alkaline amine being well known. Thus the following are some acids considered to be notably appropriate for this purpose, i.e. as examples among many that will be readily recognized as suitable for water soluble salts: Inorganic acids: hydrochloric, sulfuric, phosphoric, nitric, boric, hydroiodic, hydrofluoric, phosphotungstic. Organic acids: formic, acetic, thioacetic, acrylic, propionic, isobutyric, n-butyric, pyruvic, ethylmethylacetic, chloroacetic, dichloroacetic, methoxyacetic, alpha-bromo propionic, bromoacetic, lactic, malic, citric, malonic and glutaconic.

As also explained, some advantage is realized with insoluble acid salts, notably where a lipid-soluble compound is desired. Among others, examples of acids suitable for forming such acid salts are the following: n-caproic, n-neptoic, n-caprylic, capric, undecanoic, undecylenic, oleic, lauric,, pimelic, mandelic, salicylic, stearic, palmitic, linoleic and linolenic. Special utility may be achieved by some of these acid salts as for instance where undecylenic acid is employed, in view of the known, highly potent antifungal properties of this acid and its salts.

The remarkably high water solubility of the soluble acid salt derivatives of the invention has been established be tests of representative compounds, in comparison with the base substances. While the solubilities of the acid salts of the esters were readily determinable by the so-called dry weight method (and were so measured for the table below), the true solubilities of the base polyene antibiotics are too low, i.e. less than 0.1 milligram per milliliter, for accurate measurement by such method. Hence a more sensitive analytical method was adopted, involving ten fold dilution of the saturated water solution with an organic solvent (dimethyl sulfoxide), measurement of the ultra-violet spectrum then obtainable of the predominantly organic solution, and finally, calculation of the water solubility from the known dilution and the known (or separately determined) value of the extinction coefficient for the substance. The solubility determinations were as follows:

TABLE III

| Antibiotics and derivatives | Solubility in water, mg./ml. |
| --- | --- |
| Amphotericin B | 0.0017 |
| Amphotericin B methyl ester hydrochloride | > 75.0 |
| Amphotericin B ethyl ester hydrochloride | > 75.0 |
| Candidin | 0.116 |
| Candidin methyl ester hydrochloride | > 50.0 |
| Nystatin | 0.039 |
| Nystatin methyl ester hydrochloride | > 80.0 |
| Pimaricin | 0.052 |
| Pimaricin methyl ester hydrochloride | > 80.0 |
| Mediocidin | 0.072 |
| Mediocidin methyl ester hydrochloride | > 50.0 |
| Candicidin | 0.032 |
| Candicidin methyl ester hydrochloride | > 20.0 |
| Trichomycin | 0.046 |
| Trichomycin methyl ester hydrochloride | > 20.0 |
| Hamycin | 0.032 |
| Hamycin methyl ester hydrochloride | > 20.0 |

Although the hydrochloride salts were used for the above tests, it will be understood that in these and other respects herein, comparable properties are obtainable with addition salts made from many other acids as mentioned above, e.g. sulfates, acetates, phosphates, nitrates, and the like.

Figure 5:
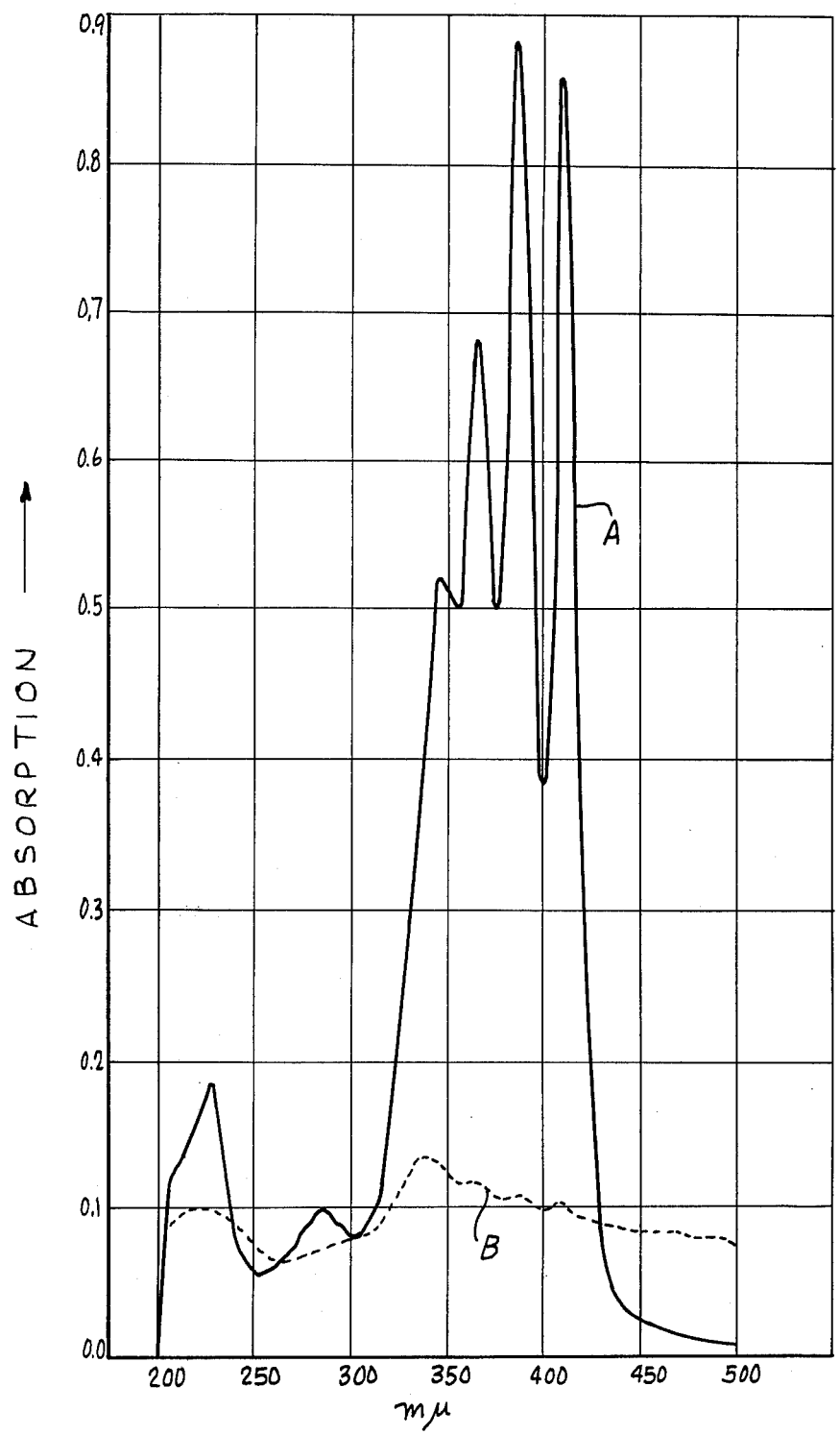
FIG. 5 is a graph showing the ultra-violet spectrum of amphotericin B methyl ester hydrochloride in water solution and also the ultra-violet spectral line for the base amphotericin B as dispersed in water.

The true solubility of the present derivatives is further illustrated by FIG. 5, where curve A is the ultraviolet spectrum for amphotericin B methyl ester hydrochloride in water, 7 micrograms per ml., and curve B is a like spectrum for the same concentration of the base amphotericin B in water. Curve A, having the same characteristic absorption peaks as the organic solvent solution of the base antibiotic and of the methyl ester in non-salt form (FIG. 4) is a true spectrum and therefore demonstrates a true solution in water, whereas curve B, lacking the characteristic configuration, shows that the base substance did not dissolve and was therefore a mere dispersion. It has previously been noted, by others, that the apparently solution-like dispersion of lyophilized amphotericin B-sodium desoxycholate in water affords only a spectral curve essentially like curve B, and this is in fact only a dispersion and is not at all a true solution.

As indicated, numerous tests have shown that the antimicrobial activity of the present derivatives, both in the immediate ester form of esterification and in the final water-soluble salt form, is substantially the same as that of the base antibiotics. Thus for example, the following table shows some of the in vitro measurements that have been made of the antifungal potency of a number of the bases and derivatives, utilizing standard methods and culture techniques, with Saccharomyces cerevisiae, an organism generally considered in the category of fungi and commonly used for a representative test of activity. In the table the numerical values represent minimum inhibitory concentration and thus the lower the value, the greater the activity in inhibiting growth of the organism.

TABLE IV

| Compounds | Min. Inhibitory Conc. micrograms/ml. Saccharomyces cerevisiae |
|---|---|
| Nystatin | 3.00 |
| Nystatin methyl ester | 4.00 |
| Amphotericin B | 0.25 |
| Amphotericin B methyl ester hydrochloride | 0.25 |
| Pimaricin | 3.50 |
| Pimaricin methyl ester | 4.00 |
| Mediocidin | 0.035 |
| Mediocidin methyl ester | 0.030 |
| Candicidin | 0.020 |
| Candicidin methyl ester hydrochloride | 0.025 |
| Trichomycin | 0.030 |
| Trichomycin methyl ester hydrochloride | 0.030 |
| Candimycin | 0.025 |
| Candimycin methyl ester | 0.025 |

In the case of amphotericin B this set of tests was extended to other microorganisms: the minimum inhibitory concentrations in micrograms per ml. for amphotericin B and its methyl ester hydrochloride respectively were 0.5 and 0.5 against *Candida albicans*, 0.5 and 0.5 against *Mucor rouxii*, and 0.20 and 0.25 against *Aspergillus niger*.

The utility of the new compounds has essentially been explained or should be self-evident in what has been said above, particularly in that they have the same biological activity as the base or parent substances and thus are in general useful for the same purposes. New utility of substantial character is apparent, as stated, by reason of special solubility characteristics. For example, use of the base antibiotics for preventing or attacking fungus infection or damage has often been unsuccessful because of lack of water solubility, e.g. with respect to inanimate articles, or to animate bodies whether plants (requiring water-base sprays) or bodies of animal nature (where the polyenes have functioned badly in internal use by reason of water insolubility); thus there has been a need for water-soluble agents, which is filled by the present invention. The water soluble derivatives have important further uses, for example in preventing or destroying fungus infection in tissue culture, where they can be employed in the same fashion and for cultivation of the same wise variety of living tissue materials, particularly including animal tissue, as explained in the above-mentioned U.S. Pat. No. 3,244,590, with superior effectiveness.

It is to be understood that the invention is not limited to the specific embodiments herein described but may be carried out in other ways without departure from its spirit.

The following is the list of literature sources to which references by item number have been made above. Items 13, 4 and 5 in this list also respectively include sources for the molecular formulas of the base antibiotics of the compounds in FIGS. 1, 2 and 3.

LITERATURE SOURCES

1. Vogel, A. I., "A Textbook of Practical Organic Chemistry, " Third Edition, Longmans, Green & Co., Ltd., London (1961), pp. 967–973.
2. Makino, K., A. Watanabe, and Y. Joh, (Jikei Univ. School of Med., Tokyo) Seikagaku, 32, 788–789 (1960).
3. Geiseler, G., and W. Koenig, Z. Physik. Chem. (Leipzig), 227(1/2), 81-92 (1964); Reimlinger, H. K., Chem. Ber., 94, 2547–2550 (1961).
4. Nystatin: Chong, C. N. and R. W. Rickards, Tetrahedron Letters, 5145–5148 (1970); and U.S. Patents Nos. 2,797,183 and 2,832,719.
5. Pimaricin: Ceder, O., Acta Chem. Scand., 18, 77–134 (1964).
6. Rimocidin: Davisson, J. W., F. W. Tanner, Jr., A. C. Finlay, and J. H. Kane, U.S. Patent 2,963,401; and Davisson, J. W., F. W. Tanner, Jr., A. C. Finlay and A. Solomons, Antibiotics & Chemotherapy, 1, 289–290 (1951).
7. Antibiotic PA-166: Koe, B. K., F. W. Tanner, Jr., K. V. Rao, B. A. Sobin, and W. D. Celmer, In: Antibiotics Annual 1957-1958, New York, Medical Encyclopedia, Inc., 1958, pp. 897–905.
8. Amphotericin A: U.S. Pat. No. 2,908,612; Gold W., H. A. Stout, J. F. Pagano, and R. Donovick, In: Antibiotics Annual 1955-1956, New York, Medical Encyclopedia, Inc., 1956, pp. 579-586; and Vandeputte, J., J. L. Wachtel, and E. T. Stiller, ibid., pp. 587–591.
9. Chromin: Wakaki, S., S. Akanabe, K. Hamada, and T. Asahina, J. Antibiotics (Japan), 5, 677-681 (1952); ibid., 6A, 145–146 (1953); ibid., 6B, 247-250 (1953).
10. Eurocidin: Arai, T., Y. Morita, and Y. Takamizawa, J. Antibiotics (Japan), 7A, 169-173 (1954); Nakazawa, K., J. Agr. Chem. Soc. Japan, 29, 650–652 (1955). [Chem. Abst., 50, 5830 (1956) ]
11. Mediocidin: Utahara, R., Y. Okami, S. Nakamura, and H. Umezawa, J. Antibiotics (Japan), 7A, 120–124 (1954).
12. Cryptocidin: Sakamoto, J. M. J., J. Antibiotics (Japan), 12A, 21-23 (1959).
13. Amphotericin B: Mechlinski, W., C. P. Schaffner, P. Ganis, and G. Avitabile, Tetrahedron Letters, 3873-3876 (1970); U.S. Patent No. 2,908,611; Gold, W., H. A. Stout, J. F. Pagano, and R. Donovick, In: Antibiotics Annual 1955–1956, New York, Medical Encyclopedia, Inc., 1956, pp. 579-586; and Vandeputte, J., J. L. Wachtel, and E. T. Stiller, ibid., pp. 587–591.
14. Levorin (Antibiotic 26/1): Borowski, E., M. Malyshkina, S. Soloviev, and T. Ziminski, Chemotherapia, 10, 176-194 (1965/66).
15. Ascosin: Hickey, R. J., C. J. Corum, P. H. Hidy, I. R. Cohen, U. F. B. Nager, and E. Kropp, Antibiotics & Chemotherapy, 2, 472–483 (1952).
16. Candicidin: Waksman, S. A., H. A. Lechevalier, and C. P. Schaffner, Bull. World Health Org., 33, 219–226 (1965); and U.S. Patent No. 2,992,162.
17. Candidin: Taber, W. A., L. C. Vining, and S. A. Waksman, Antibiotics & Chemotherapy, 4, 455-461 (1954).
18. Candimycin: Shibata, M., M. Honjo, Y. Tokui, and K. Nakazawa, J. Antibiotics (Japan), 7B, 168 (1954).
19. Hamycin: Bhate, D. S., G. R. Ambekar, K. K. Bhatnager, and R. K. Hulyalkar, Hindustan Antibiotics Bull., 3, 139–143 (1961).
20. Trichomycin: Hattori, K., J. Antibiotics (Japan), 15B, 37-43 (1962)[Chem. Abst., 58, 5532 (1963)].

21. Aureofungin: Thirumalachar, M. J., P. W. Rohalkar, R. S. Sukapure, and K. S. Gopalkrishnan, Hindustan Antibiotics Bull., 6, 108–111 (1964).
22. Protocidin: Arima, N., J. Sakamoto, and E. Okamoto, Japanese Patent No. 8648 (1960) [Chem. Abst., 55, 7758 (1961)].
23. Lucensomycin (Etruscomycin): Gaudiano, G., P. Bravo, and A. Quilico, Tetrahedron Letters, 30, 3559-3571 (1966).
24. Tetrin: Gottlieb, D. L. and H. L. Pote, Phytopathology, 50, 817-822 (1960).
25. Antibiotic PA-153: Koe, B. K., F. W. Tanner, Jr., K. V. Rao, B. A. Sobin, and W. D. Celmer, In: Antibiotics Annual 1957-1958, New York, Medical Encyclopedia, Inc., 1958, pp. 897-905.
26. Antibiotic 2814-P: Thrum, H., Naturwiss. 46, 87 (1959); and Planta Med., 8, 376 (1960).
27. Endomycin B: Vining, L. C., and W. A. Taber, Can. J. Chem., 35, 1461–1466 (1957).
28. Antibiotic PA-150 Koe, B. K., F. W. Tanner, Jr., K. V. Rao, B. A. Sobin, and W. D. Celmer, In: Antibiotics Annual 1957-1958, New York, Medical Encyclopedia, Inc., 1958, pp. 897-905.
29. Antibiotic F-17-C: Craveri, R., O. L. Shotwell, R. G. Dworschack, T. G. Pridham, and R. W. Jackson, Antibiotics & Chemotherapy, 10, 430-439 (1960).
30. Mycoheptin: Borowski, E., M. Malyshkina, T. Kotienko, and S. Soloviev, Chemotherapia, 9, 359-369 (1964).
31. Ayfactin A & B: Kaplan, M. A., B. Heinemann, I. Mydlinski, F. H. Buckwalter, J. Lein, and I. R. Hooper, Antibiotics & Chemotherapy, 8, 491-495 (1958); and British Patent No. 796,982 (1958).
32. Heptamycin: Henis, Y., N. Grossozicz, and M. Aschner, Bull. Res. Counc. Israel, 6E, VII (1957); and British Patent No. 884,713.

We claim:

1. A process of making a selected alkyl ester, wherein the alkyl group has one to three carbon atoms, of an amphoteric, polyene, macrolide antibiotic which has a macrolide ring including an uninterrupted series of 4 to 7 conjugated double bonds and which has substituents on said ring that are respectively a carboxyl group, and an amino glycoside moiety in which the amino group is primary ($-NH_2$) and which has the composition $-(C_6H_{12}O_4N)$, said process consisting in reacting said antibiotic with a reagent selected from the group consisting of diazomethane, diazoethane and diazopropane to esterify said carboxyl group in a liquid which comprises tetrahydrofurane for dissolving the selected ester and in which the ester is produced in solution.

2. A process as defined in claim 1 in which: the selected reagent is provided in solution in tetrahydrofurane; the antibiotic is provided in a liquid in which only part of the antibiotic is soluble, the remainder being undissolved; and said tetrahydrofurane solution of the reagent and said last-mentioned liquid are slowly brought together, causing the reagent to esterify the antibiotic and the tetrahydrofurane to dissolve the antibiotic as it becomes esterified.

3. A process as defined in claim 2, in which said antibiotic is first dissolved in dimethyl sulfoxide, and then tetrahydrofurane is added to complete said last above-mentioned liquid and to cause precipitation of some of the antibiotic.

4. A process as defined in claim 1, in which the produced ester of the antibiotic is separated from solution in tetrahydrofurane by treating said last-mentioned solution with ethyl ether to precipitate said produced ester, and removing the precipitated ester.

5. A process as defined in claim 1 in which the polyene macrolide antibiotic is selected from the class consisting of amphotericin B, mediocidin, candicidin, pimaricin and trichomycin.

* * * * *

UNITED STATES PATENT OFFICE
CERTIFICATE OF CORRECTION

Patent No. 4,035,568          Dated   July 12, 1977

Inventor(s)   Carl P. Schaffner et al.

It is certified that error appears in the above-identified patent and that said Letters Patent are hereby corrected as shown below:

The term of this patent subsequent to

March 23, 1993, has been disclaimed.

Signed and Sealed this thirtieth Day of August 1977

[SEAL]

Attest:

RUTH C. MASON
*Attesting Officer*

C. MARSHALL DANN
*Commissioner of Patents and Trademarks*

UNITED STATES PATENT AND TRADEMARK OFFICE
CERTIFICATE OF CORRECTION

PATENT NO. : 4,035,568

DATED : July 12, 1977

INVENTOR(S) : CARL P. SCHAFFNER and WITOLD MECHLINSKI

It is certified that error appears in the above-identified patent and that said Letters Patent are hereby corrected as shown below:

Column 1, line 40, "atoms" should read -- atom --.

Column 2, line 2, "beig" should read -- being --.

Column 3, line 29, "cheif" should read -- chief --.

Column 3, line 40, "when" should read -- then --.

Column 3, line 52, "water-soluble" should read -- water-insoluble --.

Column 4, line 9, "surfuric" should read -- sulfuric --.

Column 4, line 52, "and" should read -- of --.

Column 4, line 57, "the" should be inserted after "of" and before "nature".

Column 8, line 38, "ane" (word portion of hexaene) should be -- aene --.

Column 9, line 38, "formulation" should read -- formation --.

Column 9, line 43, "of" before "characteristic" and after "rate" should be omitted.

Column 12, line 47, "pra" should be -- para --.

Column 13, line 1, "ecognized" should be -- recognized --.

Column 13, line 7, "or" should be -- of --.

Column 13, line 50, "n-neptoic" should read -- n-heptoic --.

UNITED STATES PATENT AND TRADEMARK OFFICE
CERTIFICATE OF CORRECTION

PATENT NO. : 4,035,568
DATED : July 12, 1977
INVENTOR(S) : CARL P. SCHAFFNER and WITOLD MECHLINSKI It is certified that error appears in the above-identified patent and that said Letters Patent are hereby corrected as shown below:

Column 13, line 59, "be" should read -- by --.

Column 15, line 48, "wise" should read -- wide --.

Signed and Sealed this

Eighth Day of November 1977

[SEAL]

Attest:

RUTH C. MASON
*Attesting Officer*

LUTRELLE F. PARKER
*Acting Commissioner of Patents and Trademarks*